(12) United States Patent
Wolk

(10) Patent No.: US 6,773,567 B1
(45) Date of Patent: Aug. 10, 2004

(54) HIGH-THROUGHPUT ANALYTICAL MICROFLUIDIC SYSTEMS AND METHODS OF MAKING SAME

(75) Inventor: Jeffrey A. Wolk, Half Moon Bay, CA (US)

(73) Assignee: Caliper Life Sciences, Inc., Mountain View, CA (US)

(*) Notice: Subject to any disclaimer, the term of this patent is extended or adjusted under 35 U.S.C. 154(b) by 530 days.

(21) Appl. No.: 09/662,409

(22) Filed: Sep. 14, 2000

Related U.S. Application Data

(63) Continuation of application No. 09/267,428, filed on Mar. 12, 1999, now Pat. No. 6,148,508.

(51) Int. Cl.[7] ....................... G01N 27/26; G01N 27/447
(52) U.S. Cl. ....................... 204/604; 204/450; 204/451; 204/453; 204/600; 204/601; 422/99; 422/100
(58) Field of Search ................................. 204/450, 451, 204/453, 600, 601, 604; 422/99, 100

(56) References Cited

U.S. PATENT DOCUMENTS

| | | | |
|---|---|---|---|
| 3,551,304 A | 12/1970 | Letter et al. | |
| 4,390,403 A | 6/1983 | Batchelder | |
| 4,486,273 A | 12/1984 | Lutfy et al. | |
| 4,908,112 A | 3/1990 | Pace | |
| 5,126,022 A | 6/1992 | Soane et al. | |
| 5,429,734 A | 7/1995 | Gajar et al. | |
| 5,498,392 A | 3/1996 | Wilding et al. | |
| 5,571,410 A | 11/1996 | Swedberg et al. | |
| 5,585,069 A | 12/1996 | Zanzucchi et al. | |
| 5,593,838 A | 1/1997 | Zanzucchi et al. | |
| 5,603,351 A | 2/1997 | Cherukuri et al. | |
| 5,630,925 A | 5/1997 | Pentoney, Jr. et al. | |
| 5,635,358 A | 6/1997 | Wilding et al. | |
| 5,637,469 A | 6/1997 | Wilding et al. | |
| 5,685,965 A | 11/1997 | Allington | |
| 5,699,157 A | 12/1997 | Parce | |
| 5,750,015 A | 5/1998 | Soane et al. | |
| 5,779,868 A | * 7/1998 | Parce et al. | ................. 204/604 |
| 5,800,690 A | 9/1998 | Chow et al. | |
| 5,842,787 A | 12/1998 | Kopf-Sill et al. | |
| 5,852,495 A | 12/1998 | Parce | |
| 5,869,004 A | 2/1999 | Parce et al. | |
| 5,876,675 A | 3/1999 | Kennedy | |
| 5,880,071 A | 3/1999 | Parce et al. | |
| 5,882,465 A | 3/1999 | McReynolds | |
| 5,885,470 A | 3/1999 | Parce et al. | |
| 5,890,745 A | 4/1999 | Kovacs | |
| 6,149,787 A | * 11/2000 | Chow et al. | ................. 204/451 |

FOREIGN PATENT DOCUMENTS

| | | |
|---|---|---|
| WO | WO 9604547 | 2/1996 |
| WO | WO 9702357 | 1/1997 |
| WO | WO 9800705 | 1/1998 |

OTHER PUBLICATIONS

Dasgupta, P.K. et al., "Electroosmosis: A Reliable Fluid Propulsion System for Flow Injection Analysis," *Anal. Chem.* 66:1792–1798 (1994).

(List continued on next page.)

*Primary Examiner*—Nam Nguyen
*Assistant Examiner*—John S. Starsiak, Jr.
(74) *Attorney, Agent, or Firm*—Donald R. McKenna

(57) ABSTRACT

A method for fabricating a capillary element for electrokinetic transport of materials. The method comprises providing a first capillary element which has a first capillary channel disposed through its length. The capillary channel comprises first and second ends and an outer surface. A continuous layer of an electrically conductive material is applied along a length of the outer surface such that the continuous layer of electrically conductive material extends along the outer surface to a point proximal to, but not up to at least one of the first and second ends. The capillary element is then segmented into at least first and second separate capillary element portions at an intermediate point of the capillary element and the continuous layer.

3 Claims, 5 Drawing Sheets

OTHER PUBLICATIONS

Jacobson, S.C. et al., "Fused Quartz Substrates for Microchip Electrophoresis," *Anal. Chem.* 67:2059–2063 (1995).

Manz, A. et al., "Electroosmotic pumping and electrophoretic separations for miniaturized chemical analysis systems," *J. Micromech. Microeng.* 4:257–265 (1994).

Ramsey, J.M. et al., "Microfabricated chemical measurement systems," *Nature Med.* 1:1093–1096 (1995).

Seiler, K. et al., "Planar Glass Chips for Capillary Electrophoresis: Repetitive Sample Injection, Quantitation, and Separation Efficiency," *Anal. Chem.* 65:1481–1488 (1993).

Seiler, K. et al., "Electroosmotic Pumping and Valveless Control of Fluid Flow Within a Manifold of Capillaries on a Glass Chip," *Anal. Chem.* 66:3485–3491 (1994).

* cited by examiner

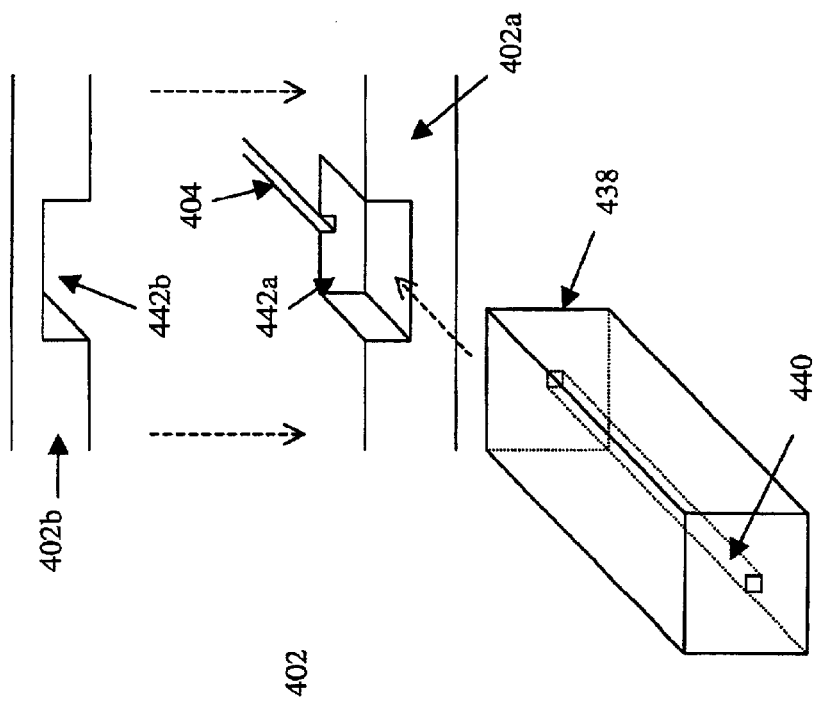
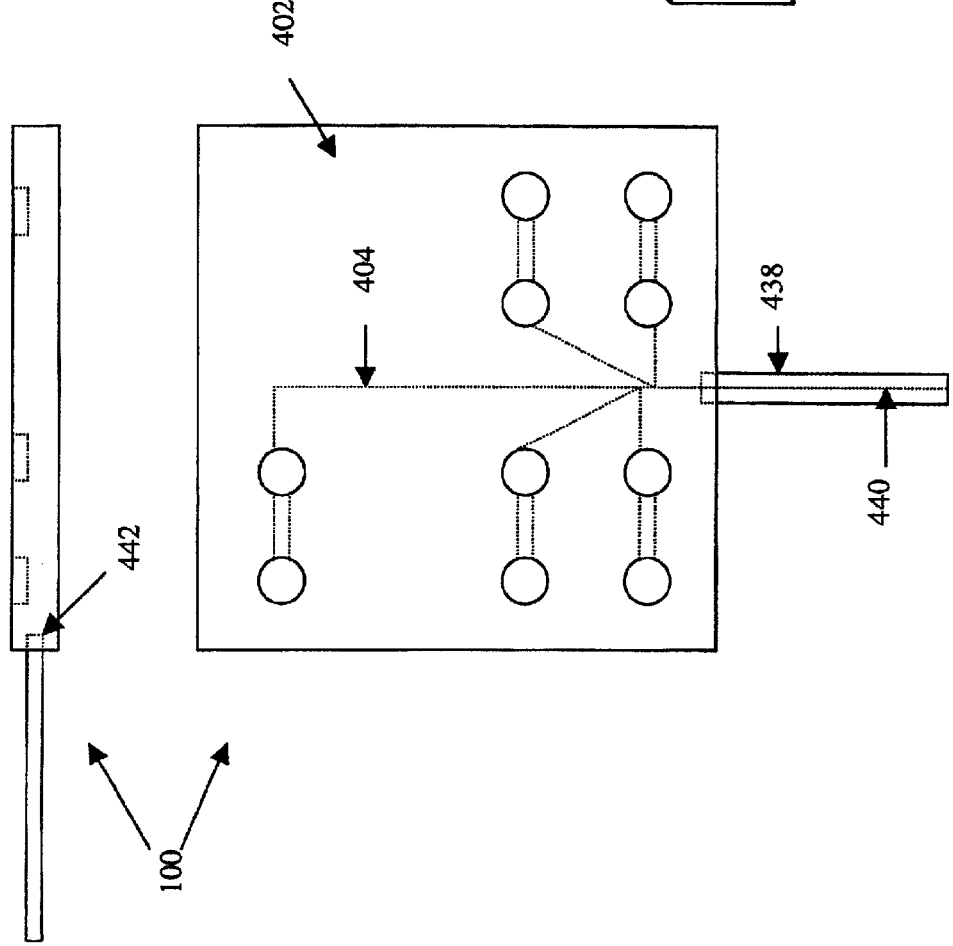
Figure 4B
Figure 4A

HIGH-THROUGHPUT ANALYTICAL MICROFLUIDIC SYSTEMS AND METHODS OF MAKING SAME

CROSS REFERENCE TO RELATED APPLICATIONS

This application is a continuation of U.S. patent application Ser. No. 09/267,428, filed Mar. 12, 1999 now U.S. Pat No 6,148,508.

BACKGROUND OF THE INVENTION

Microfluidic technology has been heralded as a significant technological advance in a number of areas, including biological research, clinical diagnostics, environmental monitoring, pharmaceutical screening, and a variety of others. The advantages associated with this technology are myriad and compelling. For example, the use of small material volumes, digitally controlled fluidics, and sensitive chemistries and detection schemes allows rapid, automatable, reproducible and accurate analytical methods in the above-described areas.

Unfortunately, some of the benefits of microfluidic technology can be difficult to realize. For example, microfluidic systems require only very small amounts of material to perform a given analysis, e.g., in the picoliter to nanoliter range. However, conventional fluid handling technologies, e.g., pipettors, pumps, dispensers and the like, typically are not capable of operating at such small volumes, generally operating above the microliter range. As a result, any advantages of reduced volumes are generally lost in introducing fluids into the microfluidic systems, because larger amounts are dispensed into reservoirs of the device.

One particularly useful method of introducing extremely small volumes of materials into the microfluidic devices is described in U.S. Pat. No. 5,779,868, which describes a pipettor capillary that is integrated with the channels of the microfluidic device. Materials are introduced into the channels of the device by sipping them through the capillary element. Using this improvement, one can readily sample nanoliter and even picoliter volumes of materials into the microfluidic system, thereby realizing this promise of microfluidics.

The present invention generally provides improved devices and methods of fabricating microfluidic systems having such a capillary element.

SUMMARY OF THE INVENTION

The present invention generally provides methods of fabricating microfluidic devices that include an external pipettor element having an integrated electrical contact/electrode. The advantages of the present invention are that the electrode is disposed up to the open terminus of the capillary element through a simple fabrication process.

In particular, provided is a method for fabricating a capillary element for electrokinetic transport of materials. The method comprises providing a first capillary element which has a first capillary channel disposed through its length. The capillary channel comprises first and second ends and an outer surface. A continuous layer of an electrically conductive material is applied along a length of the outer surface such that the continuous layer of electrically conductive material extends along the outer surface to a point proximal to, but not up to at least one of the first and second ends. The capillary element is then segmented into at least first and second separate capillary element portions at an intermediate point of the capillary element and the continuous layer. As a result, the first portion of the capillary element comprises the first end and a first intermediate end, and the second portion comprises the second end and a second intermediate end.

BRIEF DESCRIPTION OF THE FIGURES

FIG. 4 (Panels A and B) schematically illustrate an alternate configuration of the high-throughput microfluidic devices of the present invention.

DETAILED DESCRIPTION OF THE INVENTION

The present invention generally provides improved microfluidic devices and methods of fabricating microfluidic devices and systems that are useful in high throughput analysis of sample materials. In particular, the present invention is directed to improvements in the fabrication of capillary elements that are joined with the channel containing portion of the devices.

Background of Pipettor Devices

As noted above, introduction of samples into microfluidic channel networks has generally involved sacrificing one of the many promises of this otherwise promising technology. Specifically, while microfluidic systems typically are able to process fluid samples in the nanoliter range, conventional fluid handling technologies are generally limited to the microliter range; which ends up being the smallest effective volume of a sample fluid that one can use. A solution to this problem was provided in U.S. Pat. No. 5,779,868, which describes a microfluidic device having a body structure incorporating an integrated channel network for carrying out a variety of different analyses. A pipettor or capillary element is provided having a channel disposed through it such that the capillary channel is in fluid communication with at least one channel in the channel network that is disposed in the body structure. The capillary element may be a separate capillary element that is attached to the body structure, or it may be an extension of the body structure, e.g., fabricated from the same substrate as the body structure. Examples of alternative structures of such pipettor element/body structures are described in Published International Patent Application No. WO 98/00705, which is incorporated herein by reference, in its entirety for all purposes.

In one particular embodiment, electrokinetic forces are used to draw fluids or other materials into the capillary element by either or both of electrophoresis and/or electroosmosis, and then transport that material into the channel network wherein an appropriate analysis is carried out. Application of the electric fields necessary for such electrokinetic transport requires that an electrical connection be made both within the channel network, and within the reservoir of material that is to be drawn into the capillary channel and channel network. Particular methods and systems for making this latter connection include the provision of a metallic layer on the outside surface of the capillary element, e.g., by sputtering metal or applying a metallic paint on that surface, and connecting an appropriate electrical lead to that layer to deliver an appropriate voltage or current to that layer, and thus to the sample reservoir it contacts. Alternatively, a simple wire or wires are provided adjacent to or coiled around the capillary element, which function as the electrode or electrodes that contact the sample material reservoir.

Figure 1:
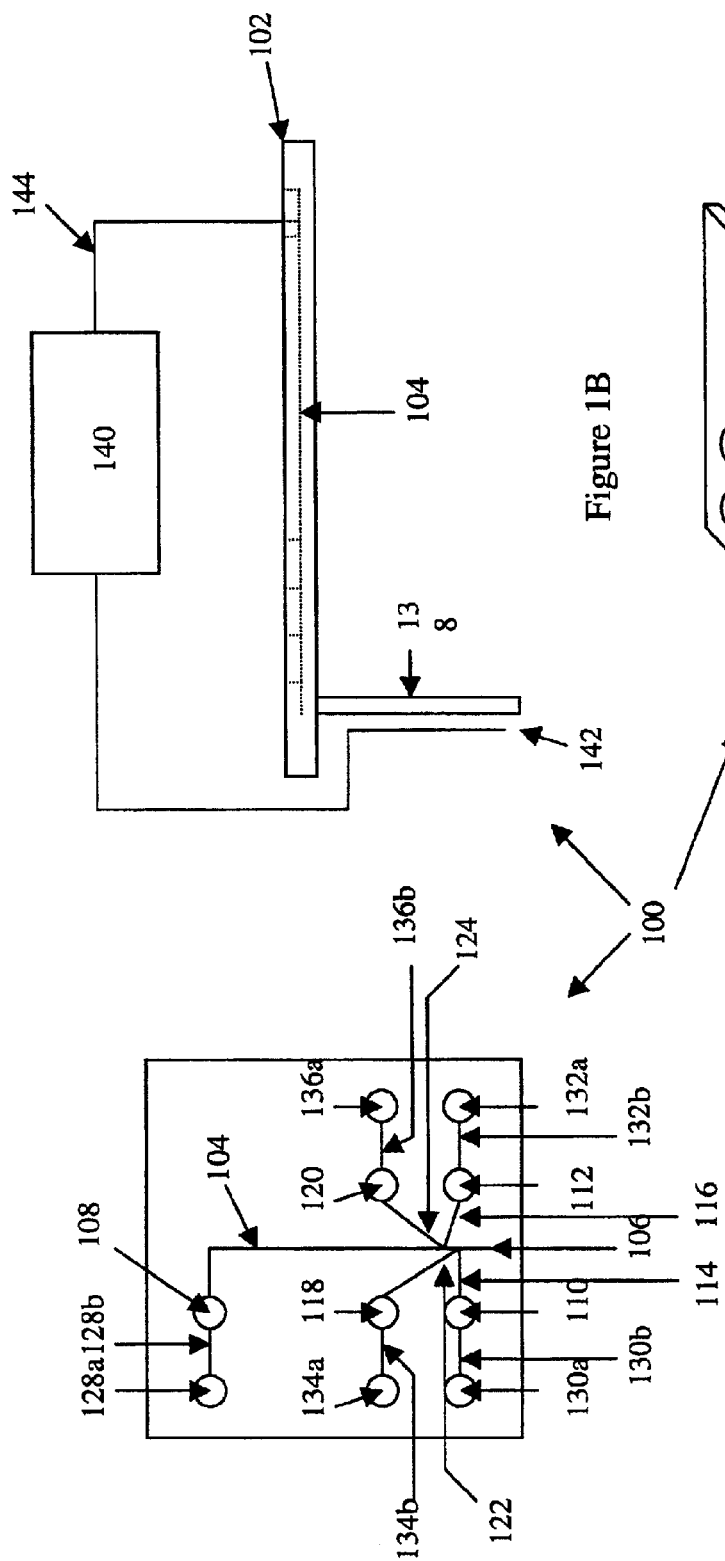
FIG. 1 illustrates a top (Panel A), side (Panel B) and perspective (Panel C) view of a high-throughput microfluidic analytical device.

An example of a previously described device is illustrated in FIG. 1. Specifically, FIG. 1 is a schematic illustration of a microfluidic device and integrated pipettor element from a top (Panel A), side (Panel B) and perspective view (Panel C). As shown, the device 100 includes a main body structure 102 that includes a channel network disposed in its interior. The channel network includes a main analysis channel 104, which fluidly connects a sample inlet 106 with waste reservoir 108. Two reagent reservoirs 110 and 112 are provided in fluid communication with the analysis channel 104 via channels 114 and 116, respectively. Reagent reservoirs 110 and 112 are paired with buffer/diluent reservoirs 118 and 120, respectively, which are in communication with channels 114 and 116 via channels 122 and 124, respectively. In order to prevent electrolytic degradation of reagent and/or buffer materials, each of reservoirs 108, 110, 112, 116 and 120 is provided in electrical and/or fluid communication with an electrical access reservoir/salt bridge channel 128a/b, 130a/b, 132a/b, 134a/b, and 136a/b, respectively. The provision of an electrical access reservoir/salt bridge allows the application of voltages via electrodes for long periods of time without resulting in substantial degradation of reagents, buffers or the like. It should be noted that as reservoir 108 is a waste well, it typically does not require a separate electrical access reservoir/salt bridge, e.g., 128a/b.

The device also includes a capillary element 138 which includes an internal capillary channel running its length, the capillary channel communicating with the analysis channel 104 via the sample inlet 106. Although shown as being perpendicular to the main body structure of the device 102, it will be appreciated that the capillary element can be coplanar with the body structure, e.g., extending in the same plane as the body structure and collinear with the analysis channel, e.g., as described in Published International Application No. WO 98/00705, which is incorporated herein by reference. Panel B of FIG. 1 also illustrates an electrical power supply 140 which provides a potential gradient between a sample reservoir into which the pipettor element is inserted and the channel network of the device, by applying different voltage levels to electrode 142, which contacts the sample fluid reservoir, e.g., a well on a multiwell plate, and electrode 144 which contacts fluid within the channel and/or reservoir network of the device.

While the methods of integrating electrodes into the high-throughput devices have proven effective for providing the appropriate electrical connection, often such electrodes are imperfect, and do not extend to the end of the capillary element. This can give rise to a number of potential problems. Initially, when an electrode doesn't extend the full length of the capillary, an adequate electrical connection with the fluid reservoir requires inserting the capillary element further into the reservoir.

A more typical problem is that upon removal of the capillary and electrode from the sample material, flow of material through the capillary element into the channel network is stopped, because the electrical circuit is broken. Thus, in high throughput systems where multiple different samples are drawn serially into the capillary channel and channel network, e.g., from different wells in a multiwell plate, the flow of material is intermittently started and stopped. Further, in order to ensure that all materials are subject to the same conditions, other materials flowing through the remainder of the channel network must be started and stopped. In addition to the problems this causes for the assay biochemistry, it also represents a substantial time waste, in that the time spent transitioning between sample reservoirs is effectively lost, i.e., nothing is being analyzed.

Devices fabricated according to the presently described methods, however, remedy many of these problems. In particular, in accordance with the fabrication methods described herein a first capillary element is provided which includes the capillary channel disposed through its length. As noted previously, this capillary element may be separate or integral to the body structure of the channel network of the device.

A continuous layer of an electrically conductive material is applied along a length of the outer surface of the capillary element. By "continuous layer" is meant that a layer of material is continuous along the length of the capillary element. The layer may or may not be continuous around the circumference or perimeter of the capillary element, e.g., it can be a uniform coating of the capillary element or it can be a simple stripe applied down the length of the capillary.

The electrically conductive layer is typically applied to a point that is proximal to at least, and in some cases, both ends of the capillary element. By "proximal to" is meant that the conductive layer typically extends to a point that is within about 5 mm, typically within about 2 mm, preferably within about 1 mm of the end of the capillary element, more preferably within about 0.5 mm and often within about 0.2 mm or even 0.1 mm of the end of the capillary.

Generally, a small amount of open space is left at the end of the capillary element, in order to permit insertion of the capillary element into the body structure of the overall device, if appropriate to the chosen fabrication method. Depending upon the method used, the uncoated ends may be protected from coating by masking off the ends of the outer surface of the capillary element using a protective layer, e.g., tape or other covering.

Typically, the conductive layer may be applied by any of a variety of methods that are well known in the art for metalizing surfaces. For example, a metallic layer may be sputtered onto the outer surface of the capillary. Alternatively, a thin metallic sheet or foil may be applied around the capillary element, which, in turn may be thermally or adhesively bonded to the outer surface. Whether sputtered, wrapped or otherwise, typically preferred metallic layers are generally selected from those metals that are widely used in electronics applications, including, e.g., platinum, chrome, titanium, tungsten, and rhodium. In a further alternative method, a metallic or electrically conductive paint is simply painted onto the outer surface of the capillary element.

The capillary element is then cut or otherwise segmented at an intermediate point along the length of the capillary and within the continuous layer. Typically, this segmenting is carried out by any of a number of means, including, e.g., sawing, scoring and breaking, or the like. By cutting or segmenting the capillary at an intermediate point in the conductive layer, a new end is created, which has the conductive layer extending up to that end. This end is then employed as the sampling end of the ultimate capillary element. In particular, in the case of a separate capillary element that is attached to the body structure, the original end with the conductive layer extending up to a point proximal to the end, is the end that is attached to the body structure. This is typically accomplished by inserting the capillary element into an aperture in the body structure that is configured to receive the capillary.

Figure 2:
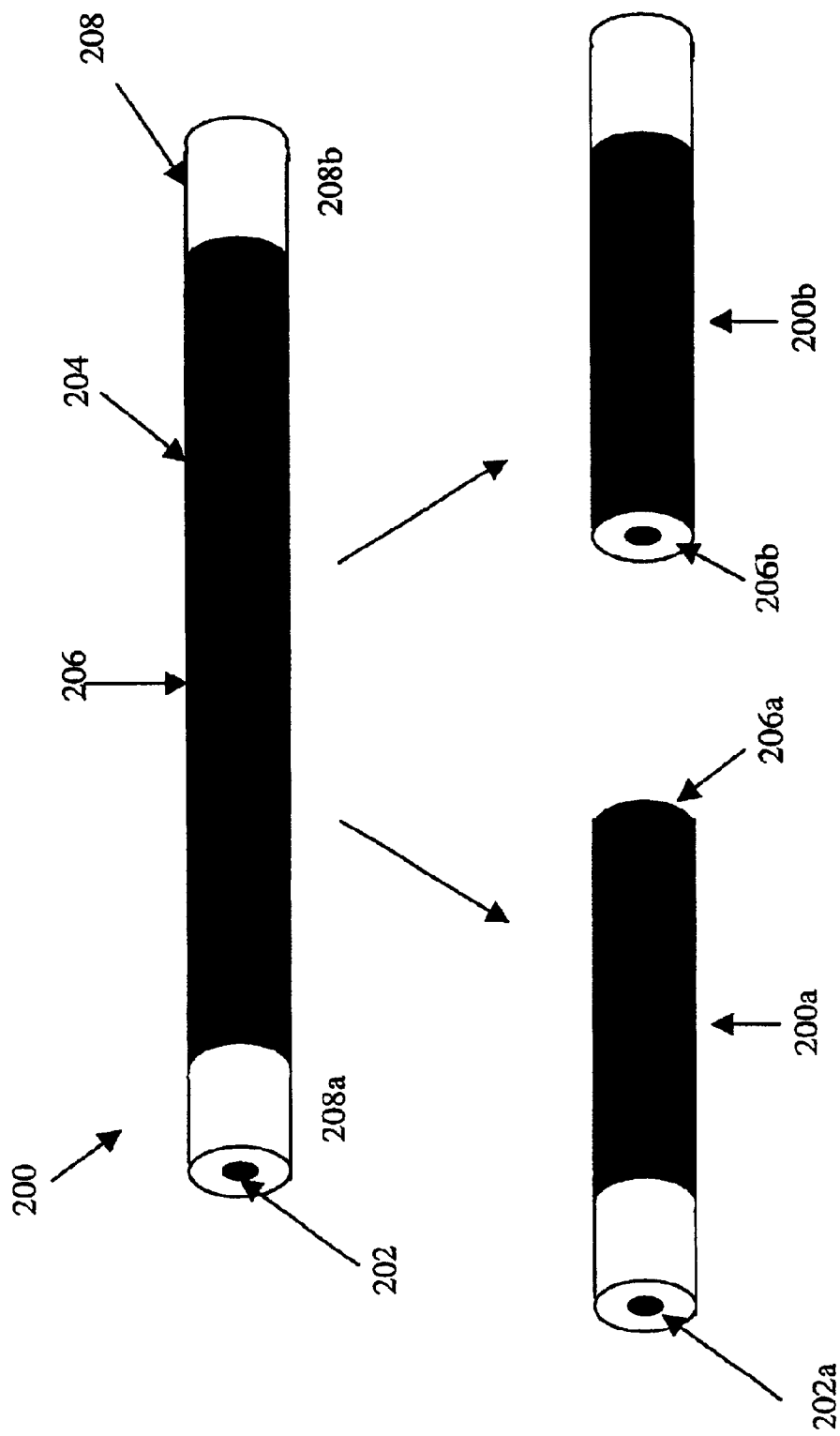
FIG. 2 schematically illustrates the fabrication of a pipettor element in accordance with the present invention.

This process is schematically illustrated in FIG. 2, where an initial capillary element 200 having a capillary channel 202 disposed through it is provided with a continuous layer 204 of conductive material deposited upon its outer surface 208. Although shown as a cylindrical capillary, it will be appreciated that any capillary shape can be used in accordance with the methods described herein, including rectangular, polygonal, e.g., octagonal, etc., elliptical, and amorphous. The layer of conductive material extends substantially the entire length of the capillary, but not the entire length. In particular, outer surface portions 208a and 208b are left uncoated by the conductive layer. By not coating the capillary element 200 up to the end, one reduces the chances of fouling the open end of the capillary with the coating. The capillary element 200 is segmented at intermediate point 206, which as shown, produces two capillary portions 200a and 200b each having an intermediate end 206a and 206b, respectively, which has the conductive layer 204 extending up to it.

Figure 3:
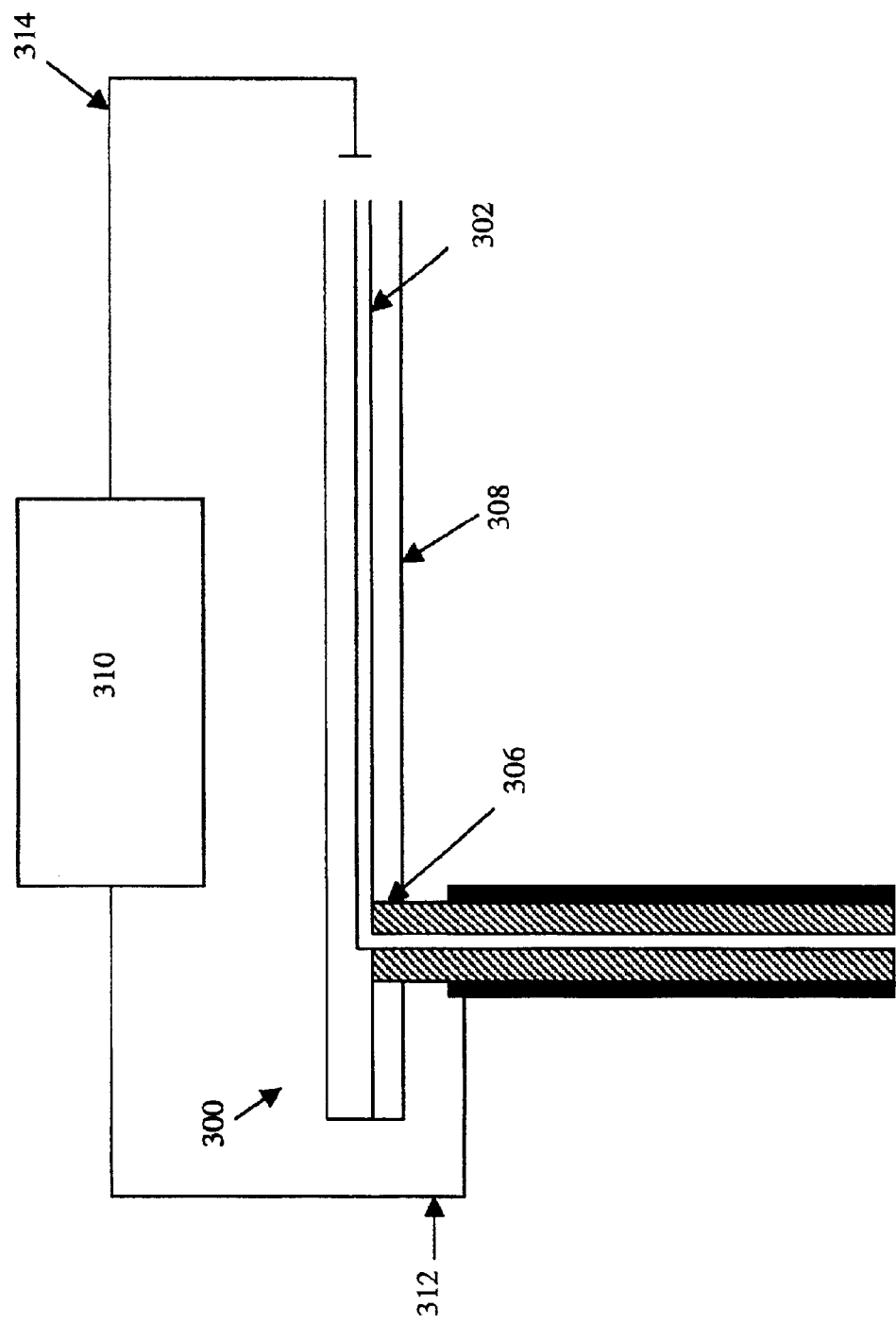
FIG. 3 schematically illustrates the pipettor element shown in FIG. 2 in conjunction with a microfluidic channel network, which functions as a high-throughput microfluidic analytical device.

Attachment of the capillary element to the body structure, if such is the structure of the device, is generally carried out by providing a hole or aperture that approximates the size of the capillary element, e.g., the outer circumference or perimeter, such that the capillary can be inserted into the hole. Typically, the hole or aperture is dimensioned to receive the capillary element, and thus is slightly larger than he capillary element. Thus, for circular capillaries, this hole or aperture may be provided by drilling into the body structure of the device using, e.g., an ultrasonic or high-speed drill. The hole is positioned such that when the capillary is inserted into it, the capillary channel is in fluid communication with at least one of the channels within the body structure. FIG. 3 schematically illustrates the junction of a microfluidic device 300 containing a channel network 302 with a capillary element 200a having an outer coating 204 which extends up to the end 206a of the capillary, as described with reference to FIG. 2. As shown, the uncoated end 202a of the capillary element 204a is inserted into a hole 306 that is disposed in the body structure 308 of the device 300, such that the channel 202 of the capillary element 200a is in fluid communication with the channel network 302. As noted above, fabrication of the hole or aperture into which the capillary element is inserted, may be accomplished by a number of means. Typically, for example, for cylindrical capillaries, this aperture is drilled into the substrate or body structure at an appropriate point, e.g., to provide for connection between the capillary element and the channel network. Alternative microfabrication methods are also useful, including, e.g., etching the aperture or fabricating the body structure, e.g., by injection molding, embossing, stamping or other methods, to include the aperture.

FIG. 3 also schematically illustrates an electrical controller attached to conductive layer 204 via electrical lead 312, and in electrical communication with fluid in the reservoirs or channels of channel network 302 via electrode/electrical lead 314.

Alternatively, rectangular capillary elements may be used. In such cases, the hole or aperture may be provided by etching a square or rectangular aperture into the body structure such that the capillary is appropriately positioned. Such rectangular capillary elements are described in, e.g., U.S. patent application Ser. No. 09/173,469, filed Oct. 14, 1998, which is incorporated herein by reference for all purposes.

An example of a device similar to that shown in FIG. 1, but including a collinear, substantially rectangular capillary element, is shown in FIG. 4A. The same reference numerals are used for elements that are common between FIGS. 1 and 4. As shown, the overall device 100 again includes a main body structure 102 as described with reference to FIG. 1, which includes integrated channel network disposed in its interior. The rectangular capillary element 438 includes a capillary channel 440 running its length. The capillary element is attached to the body structure via a rectangular opening 442 in the body structure 102. Insertion of a rectangular end of the capillary element 438 into rectangular opening 442 places the capillary channel 440 into fluid communication with at least one of the channels in the integrated channel network within the body structure.

Because the opening 442 in the body structure is substantially rectangular, it is more conveniently fabricated than circular openings. In particular, while circular openings are typically drilled or air abraded into a body structure, rectangular openings are more conveniently fabricated by fabricating rectangular notches in two substrates by, e.g., photolithographic methods, which are mated to define the body structure of the device. The two notches are positioned to provide a single rectangular opening in the body structure. FIG. 4B illustrates an expanded view of the joining of a rectangular capillary with a two-layer microfluidic device. As shown, the device comprises a two-layer body structure including the above-described notches. As shown, the body structure 102 is made up of at least first and second planar substrates 402a and 402b, respectively. The upper surface of the lower substrate 402a includes grooves fabricated therein, which correspond to the desired channel structure of the finished device, e.g., groove 404. The upper substrate 402b is mated and bonded to the upper surface of the lower substrate 402a (as illustrated by the dashed arrows). Typically, bonding is carried out by thermal bonding techniques, which result in a single integrated unit having sealed channels or conduits running through its interior. The upper substrate also typically includes a number of holes disposed through it (not shown), which holes align with and provide access to the channels of the finished device. The lower and upper substrates also include notches 442a and 442b, respectively, which are aligned when the two substrates are mated, to define an opening. Although these notches could be of any shape, e.g., rectangular, hemispherical, trapezoidal, etc., it is generally easier to fabricate substantially rectangular notches, e.g., using the same fabrication techniques and steps used in fabricating the grooves/channels of the device 100, e.g., groove 404. Substantially rectangular notches produce a substantially rectangular opening along the edge of the body structure of the device. The notches generally range in depth depending upon the dimensions of the rectangular capillary element to be inserted therein. Typically, however, these notches will range in depth from about 10 $\mu$m to about 50 $\mu$m, and will be fabricated to make the transition from the channel in the capillary element to the channel in the device's body structure. For example, where a capillary element has a wall thickness of 15 $\mu$m (e.g., minor axis or interior diameter of 15 $\mu$m, with wall thickness of 15 $\mu$m yielding overall cross section of 45 $\mu$m), the notch 442a on the lower substrate 402a will typically be approximately 30 µm deep, e.g., allowing for 15 µm wall thickness and a 15 µm deep channel which matches up with the minor axis of the capillary element, while the notch 442b on the upper substrate 402b will be approximately 15 µm deep to accommodate the upper wall of the capillary element. The notches typically extend into the substrate, e.g., away from the edge, up to about 2 mm, in order to conveniently and fixedly receive the capillary element.

A substantially rectangular capillary element 438 is then inserted and attached to the body structure 402 via the opening (as shown by the dashed arrow). Typically, attachment of the capillary element is accomplished using an adhesive, e.g., epoxy, although other bonding techniques may also be used depending upon the nature of the materials used, e.g., thermal bonding, solvent welding, etc.

Although the capillary element 438 is shown as being collinear with the main analysis channel 404 of the device 100, it will be readily apparent that the rectangular capillary element can be curved or bent out of the plane of the channel network to provide a more useful sampling capillary. Bent capillaries can be held in the bent shape, e.g., by applying a rigid bent sheath, i.e., plastic sheath or a coated sheath of polyimide or Teflon (polytetrafluoroethylene) or the like, over the capillary element to hold the capillary in the bent or curved orientation. Alternatively, a rectangular capillary can extend out of the plane of the channel network, e.g., perpendicular to the channel network plane, e.g., as shown in FIG. 1. In particular, rectangular openings could be readily fabricated into the lower substrate 402a using well known fabrication techniques, e.g., etching.

In a further alternative method, the capillary element may comprise merely an extension of the body structure of the device itself, through which a channel has been provided. The fabrication of such a capillary element is generally carried out as described in published International Patent Application No. 98/00705, which is incorporated herein by reference. In the case of devices fabricated in this way, the methods of the present invention are still practical. Specifically, the conductive layer is provided over the outer surface of the capillary element portion of the device, extending up to a point proximal to the open end of the capillary portion. The capillary portion is then cut or chopped at an intermediate point in the conductive layer, creating a new end of the capillary element, wherein the conductive layer extends up to the new end of the capillary.

Following assembly of the overall device, an electrical lead that is either coupled to or connectable to an electrical power source, is connected to the conductive layer on the capillary element, in order to deliver an appropriate voltage or current through that layer. Connecting the electrical lead is generally carried out by methods known in the art, e.g., soldering, or adhesively attaching the lead.

As noted above, the devices fabricated according to the methods described herein provide a number of advantages. For example, by providing the conductive layer extending to the sampling end of the capillary element, one is able to maintain an electrical circuit through the capillary channel for a greater amount of time. In particular, the electrical circuit is established substantially from the moment the capillary element contacts the fluid it is sampling, without dipping the capillary deeper into the well. This permits sampling the material with a smaller likelihood of contamination from previously sampled materials, as well as faster sampling, by not requiring.

Figure 5:
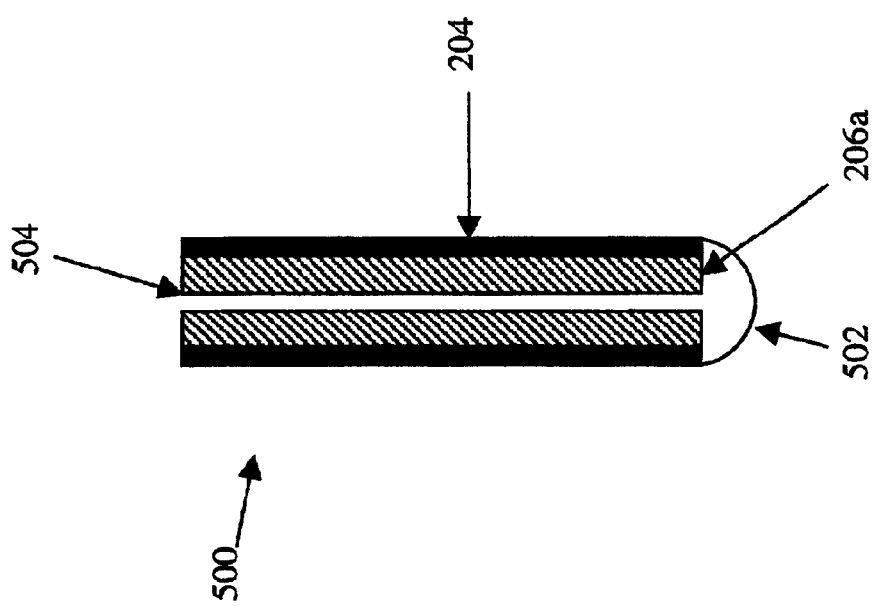
FIG. 5 schematically illustrates the interaction of capillary elements as described herein with fluids which are being drawn into the capillary.

In addition, the conductive layer permits the maintaining of the electrical circuit even after the capillary element is withdrawn from the sampled fluid. Specifically, once the capillary element is withdrawn from the sample fluid, a drop remains on the tip of the capillary element, e.g., as shown in FIG. 5 and with reference to FIGS. 2 and 3. As the drop of fluid 502 extends across the surface of capillary end 206a of the capillary element 500, it will maintain the electrical circuit between the conductive layer 204 and the fluid in the capillary channel 504. By maintaining the electrical circuit, even while the capillary is out of the sample or other fluid reservoir, one can maintain flow of material through the capillary channel, as well as the remainder of the channel network. As noted above, this can amount to a substantial time savings in high throughput systems which require frequent movement of the capillary element from one fluid reservoir to another.

As an example, assuming that an assay employs a set of spacer fluids between each sample plug that includes a low salt space with high salt guard bands on each side of the sample plug, e.g., as described in WO 98/00705, previously incorporated herein each sampling cycle requires that the capillary element make four well to well shifts, during which time the assay operation would typically be suspended. If each shift requires one second, then four seconds are lost during each cycle. For a 96 well plate, this amounts to nearly six and a half minutes. Assuming that one is screening a modest library of 10,000 different compounds, the time waste amounts to approximately eleven hours. By maintaining the electrical circuit intact during these transition periods, as is possible using the methods described herein, one can recover these time losses.

Although generally described with reference to the fabrication of capillary element containing microfluidic devices, it will be appreciated that the methods described herein have use in any instance where one wishes to provide an integrated electrical connection to the very end of a capillary element, e.g., as a ring electrode, or the like.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A microfluidic device, comprising:
   a body structure having at least a first microscale channel disposed therein;
   a capillary element having first and second ends and a capillary channel disposed therethrough, the first end of the capillary element being attached to the body structure whereby the capillary channel is in fluid communication with the at least first microscale channel; and
   a conductive layer deposited on at least a portion of a surface of the capillary element, the conductive layer extending from a point proximal to the first end of the capillary element up to the second end of the capillary element, wherein the capillary element is attached to the body structure by the first end being inserted into an aperture in the body structure.

2. The microfluidic device of claim 1, wherein the conductive layer is deposited along a portion of a length of the capillary element that extends to a point proximal to but not up to the first end of the capillary element.

3. A microfluidic device, comprising:

a body structure having at least a first microscale channel disposed therein;

a capillary element having first and second ends and a capillary channel disposed therethrough, the first end of the capillary element being attached to the body structure whereby the capillary channel is in fluid communication with the at least first microscale channel; and a conductive layer deposited on at least a portion of a surface of the capillary element, the conductive layer extending from a point proximal to the first end of the capillary element up to the second end of the capillary element, wherein the capillary element is substantially rectangular.

* * * * *